United States Patent

Shick et al.

Patent Number: 5,837,274
Date of Patent: Nov. 17, 1998

[54] AQUEOUS, ANTIMICROBIAL LIQUID CLEANING FORMULATION

[75] Inventors: Richard L. Shick, Alpharetta, Ga.; Claude R. Wheeler, Jr., Philadelphia, Pa.

[73] Assignee: Kimberly Clark Corporation, Neenah, Wis.

[21] Appl. No.: 735,039

[22] Filed: Oct. 22, 1996

[51] Int. Cl.[6] ................................ A01N 25/32
[52] U.S. Cl. ................ 424/406; 424/405; 424/78.07
[58] Field of Search ................... 424/405, 406, 424/78.05, 78.07

[56] References Cited

U.S. PATENT DOCUMENTS

| | | | |
|---|---|---|---|
| 3,235,446 | 2/1966 | Shelanski et al. | 424/405 |
| 3,284,362 | 11/1966 | Zussman | 252/107 |
| 3,445,398 | 5/1969 | Jungermann et al. | 252/107 |
| 3,506,720 | 4/1970 | Model et al. | 260/613 |
| 3,625,904 | 12/1971 | Nosler et al. | 252/107 |
| 3,700,601 | 10/1972 | Hilden | 252/105 |
| 3,723,326 | 3/1973 | Cheng et al. | 252/107 |
| 3,725,547 | 4/1973 | Kooistra | 424/245 |
| 3,800,048 | 3/1974 | Model et al. | 424/304 |
| 3,875,071 | 4/1975 | Grand | 252/106 |
| 3,897,357 | 7/1975 | Carmello et al. | 252/106 |
| 3,904,696 | 9/1975 | Model et al. | 260/613 R |
| 3,925,227 | 12/1975 | Corey et al. | 252/106 |
| 3,956,489 | 5/1976 | Molnar | 424/233 |
| 3,968,210 | 7/1976 | Schenkel | 424/235 |
| 3,970,576 | 7/1976 | Carmello et al. | 252/106 |
| 3,982,022 | 9/1976 | Hool et al. | 424/341 |
| 3,989,827 | 11/1976 | Apostolatos et al. | 424/235 |
| 4,057,648 | 11/1977 | Hool et al. | 424/341 |
| 4,082,852 | 4/1978 | Heiss | 424/317 |
| 4,098,877 | 7/1978 | Ball et al. | 424/45 |
| 4,111,844 | 9/1978 | Polony et al. | 252/106 |
| 4,118,332 | 10/1978 | Apostolatos et al. | 252/107 |
| 4,235,733 | 11/1980 | Watanabe et al. | 252/107 |
| 4,282,110 | 8/1981 | Koike | 252/107 |
| 4,312,855 | 1/1982 | Grand | 424/59 |
| 4,322,308 | 3/1982 | Hooper et al. | 252/107 |
| 4,323,466 | 4/1982 | Curry et al. | 252/106 |
| 4,339,462 | 7/1982 | Muntwyler et al. | 424/341 |
| 4,490,280 | 12/1984 | Joshi et al. | 252/368 |
| 4,762,642 | 8/1988 | Joshi et al. | 252/368 |
| 4,764,365 | 8/1988 | Boothe et al. | 424/81 |
| 4,832,861 | 5/1989 | Resch | 252/106 |
| 4,954,281 | 9/1990 | Resch | 252/107 |
| 4,971,800 | 11/1990 | Chess et al. | 424/449 |
| 4,975,218 | 12/1990 | Rosser | 252/117 |
| 5,006,529 | 4/1991 | Resch | 514/721 |
| 5,045,317 | 9/1991 | Chess et al. | 424/401 |
| 5,051,260 | 9/1991 | Chess et al. | 424/449 |
| 5,147,574 | 9/1992 | MacGilp et al. | 252/108 |
| 5,158,699 | 10/1992 | MacGilp et al. | 252/132 |
| 5,234,618 | 8/1993 | Kamegai et al. | 252/106 |
| 5,296,157 | 3/1994 | MacGilp et al. | 252/108 |
| 5,296,158 | 3/1994 | MacGilp et al. | 252/108 |

(List continued on next page.)

FOREIGN PATENT DOCUMENTS

| | | |
|---|---|---|
| 4243469A | 6/1994 | Germany . |
| 94/17166 | 8/1994 | WIPO . |

OTHER PUBLICATIONS

"Interaction Between Cosmetic Ingredients and Preservatives", *Cosmetics & Toiletries* Magazine, vol. 110, Nov. 1995, pp. 81–86.

Primary Examiner—Neil S. Levy
Attorney, Agent, or Firm—Karl V. Sidor

[57] ABSTRACT

An aqueous, antimicrobial liquid cleaning formulation including: 1) a polymeric deposition aid composed of a mixture of liquid, hydroxyl-terminated urethane polymers in polyethylene glycol; 2) a phenol derivative antimicrobial agent; and 3) a surfactant system comprising predominantly nonionic surfactants, amphoteric surfactants or combinations thereof such that the liquid cleaning formulation provides at least about 10 percent greater antimicrobial activity than the same formulation without the polymeric deposition aid.

19 Claims, 5 Drawing Sheets

U.S. PATENT DOCUMENTS

| | | | |
|---|---|---|---|
| 5,306,486 | 4/1994 | McCook et al. | 424/59 |
| 5,348,678 | 9/1994 | Hodam, Jr. et al. | 424/405 |
| 5,356,803 | 10/1994 | Carpenter et al. | 435/200 |
| 5,372,744 | 12/1994 | Kamegai et al. | 252/174.17 |
| 5,407,958 | 4/1995 | Heath et al. | 514/546 |
| 5,417,875 | 5/1995 | Nozaki | 252/106 |
| 5,439,681 | 8/1995 | Khan et al. | 424/400 |
| 5,449,763 | 9/1995 | Wulff et al. | 536/18.6 |
| 5,512,199 | 4/1996 | Khan et al. | 252/106 |
| 5,516,510 | 5/1996 | Beilfuss et al. | 424/65 |

AQUEOUS, ANTIMICROBIAL LIQUID CLEANING FORMULATION

FIELD OF THE INVENTION

The present invention relates to liquid formulations for personal cleaning that have antimicrobial activity.

BACKGROUND

It is well known that certain types of surfactants tend to inhibit desirable antimicrobial activity of some antimicrobial agents derived from phenol. Exemplary phenol derivative antimicrobial agents include, for example, triclosan, phenoxyethanol, chloroxylenol, o-phenylphenol and o-phenylphenate and the like. Nonionic and cationic surfactants have been identified as having a particularly negative influence on antimicrobial activity. Their activity is stated to be highly dependent on the pH of the system. The effect of some of these surfactants may be so great as to completely eliminate most measurable antimicrobial activity.

In view of this, many aqueous, antimicrobial liquid formulations for personal cleaning contain other surfactants and compounding additives that strive to minimize interfering with antimicrobial activity of phenol derivative antimicrobial agents. However, even these surfactants and compounding additives may cause some reduction in the activity of phenol derivative antimicrobial agents.

Another problem is that anionic and cationic surfactants tend to be harsher and less desirable for skin contact than nonionic surfactants. Thus, conventional aqueous liquid cleaning formulations having desirable levels of antimicrobial activity also have the potential to cause skin irritation if used frequently because mild surfactants are omitted to preserve the activity of phenol derivative antimicrobial agents.

This takes on greater importance if the aqueous liquid cleaning formulations are used several times a day or more. Frequent washing is associated with many environments including, but not limited to, hospitals, clinics, infant care and child care centers, medical and biological laboratories, food service facilities, restaurants, and some industrial manufacturing sites.

Accordingly, there is a need for an aqueous, antimicrobial liquid cleaning formulation including a phenol derivative antimicrobial agent and a mild surfactant system composed predominately of one or more nonionic surfactants, amphoteric surfactants or combination thereof which provides adequate antimicrobial activity and avoids irritating skin with frequent use. This need extends to such a formulation that provides at least about 10 percent greater antimicrobial activity in combination with less erythema as determined by the Arm Wash Test than conventional formulations containing predominantly anionic and/or cationic surfactants.

Meeting these needs is important because frequent hand washing in medical and other environments has been shown to reduce the transmission of dangerous pathogens and infections.

SUMMARY OF THE INVENTION

The problems described above are addressed by the present invention which provides an aqueous, antimicrobial liquid cleaning formulation composed of: 1) a polymeric deposition aid comprising a mixture of liquid, hydroxyl-terminated urethane polymers in polyethylene glycol; 2) a phenol derivative antimicrobial agent; and 3) a surfactant system composed predominantly of non-ionic surfactants, amphoteric surfactants and/or combinations thereof such that the liquid cleaning formulation provides at least about 10 percent greater antimicrobial activity than the same formulation without the polymeric deposition aid. The formulation may further include one or more conventional formulating components.

According to the invention, the surfactant system is composed predominantly of non-ionic surfactants, amphoteric surfactants and/or combinations thereof but may include small amounts of other surfactants (e.g., anionic surfactants and/or cationic surfactants) if their presence does not provide significant adverse consequences to the mildness of the formulation.

The polymeric deposition aid is a hydroxy terminated urethane compound having the general formula:

wherein R is selected from an alkylene or alkenylene radical containing from one to about 20 carbon atoms, a cycloalkylene or cycloalkenylene radical containing from about 5 to about 10 carbon atoms, a mononuclear or fused ring arylene radical containing from about 6 to about 10 carbon atoms, unsubstituted or substituted with one or more lower alkyl, lower alkoxy, nitro or amino groups or halogen atoms, wherein R' is the same or different alkylene or alkenylene radical, wherein m is an integer selected to provide an (O—R') moiety having molecular weight of from about 40 to about 6000, and wherein n and n' are the same or different integers of from 0 to about 30 inclusive, correlated with m so as to provide a hydroxy-terminated urethane compound having a molecular weight of up to about 200,000.

It is desirable that m is an integer selected to provide an (O—R') moiety having molecular weight of from about 40 to about 60. More desirably, n and n' are the same or different integers of from 0 to about 30 inclusive, correlated with m so as to provide a hydroxy-terminated urethane compound having a molecular weight of up to about 1,800.

According to an embodiment of the invention, the polymeric deposition aid is poly(oxy-1,2-ethanediyl),α-hydro-ω-hydroxy-, polymer with 1,1'-methylene-bis-(4,isocyanato-cyclohexane). Desirably, the phenol derivative antimicrobial agent is 2,4,4'-trichloro-2'-hydroxy diphenyl ether. One or more of the conventional formulating component may be selected from carriers, preservatives, humectants, emollients and combinations thereof.

The aqueous, antimicrobial liquid cleaning formulation of the present invention provides at least about 20 percent greater antimicrobial activity than the same formulation without the polymeric deposition aid. In another aspect of the present invention, the formulation provides at least about 10 percent greater antimicrobial activity in combination with less skin irritation or erythema as determined by the Arm Wash Test than conventional formulations containing predominantly anionic surfactants. In yet another aspect of the invention, the liquid cleaning formulation provides at least about 10 percent greater antimicrobial activity in combination with at least about 10 percent less incidence of dermal erythema as determined by the Arm Wash Test than conventional formulations containing predominantly anionic surfactants. For example, the liquid cleaning formulation may provide at least about 10 percent greater antimicrobial activity in combination with at least about 15 percent less incidence of dermal erythema as determined by the Arm Wash Test than conventional formulations containing predominantly anionic surfactants.

DETAILED DESCRIPTION

The present invention encompasses an aqueous, antimicrobial liquid cleaning formulation. An important feature of the aqueous, antimicrobial liquid cleaning formulation of the present invention is that it utilizes predominantly nonionic and/or amphoteric surfactants in combination with phenol derivative antimicrobial agents to provide a liquid cleaning formulation that is mild to the skin yet has satisfactory antimicrobial activity. While it is desirable to use predominantly nonionic and amphoteric surfactants in liquid cleaning formulations, these surfactants tend to have a strong negative impact on the antimicrobial activity of phenol derivative antimicrobial agents. Some of these surfactants essentially eliminate antimicrobial activity. The present invention provides a liquid cleaning formulation including phenol derivative antimicrobial agents in combination with predominantly nonionic and/or amphoteric surfactants such that the formulation has useful levels of antimicrobial activity. Of course, it should be understood that the present invention contemplates formulations containing predominantly nonionic and/or amphoteric surfactants balanced with relatively small amounts of anionic and/or cationic surfactants such that the presence of the anionic and/or cationic surfactants does not affect the mildness of the formulation.

It is important to be aware of the distinction between aqueous, antimicrobial liquid cleaning formulations used for washing and emulsion compositions used to cleanse, treat or condition skin.

Generally speaking, aqueous, antimicrobial liquid cleaning formulations refer to detergent-based, antibacterial "liquid soaps" used for washing skin (e.g., hand-washing, bathing, showering, or the like). The formulations are typically applied to the skin (with or without water), worked into a lather, and then rinsed off the skin with water. Exemplary detergent-based liquid soaps of this type include Lever 2000® antibacterial liquid soap (Lever Brothers) and Dial® antibacterial liquid soap (Dial Corporation). Frequent, repeated use of these aqueous, antimicrobial liquid cleaning formulations have a tendency to cause erythema and skin irritation.

In contrast, emulsion compositions are generally used to cleanse, treat and/or condition the skin. Such emulsion compositions are oil-in-water emulsions used to deposit certain ingredients on the skin from the oil phase of the oil-in-water emulsion. These oil-in-water emulsions are usually in the form of a cream, lotion or the like. It is generally thought that such oil-in-water emulsions have little or no tendency to cause erythema and skin irritation and, in some cases, are actually used to treat skin irritation.

The aqueous, antimicrobial liquid cleaning formulation of the present invention is composed of: 1) a polymeric deposition aid comprising a mixture of liquid, hydroxyl-terminated urethane polymers in polyethylene glycol; 2) a phenol derivative antimicrobial agent; 3) a surfactant system composed predominantly of non-ionic surfactants, amphoteric surfactants or combinations thereof such that the liquid cleaning formulation provides at least about 10 percent greater antimicrobial activity than the same formulation without the polymeric deposition aid. Embodiments of the present invention may also contain one or more conventional formulating components including, but not limited to, carriers, preservatives, humectants, emollients and combinations thereof.

The polymeric deposition aid is a hydroxy terminated urethane compound having the general formula:

wherein R is selected from an alkylene or alkenylene radical containing from one to about 20 carbon atoms, a cycloalkylene or cycloalkenylene radical containing from about 5 to about 10 carbon atoms, a mononuclear or fused ring arylene radical containing from about 6 to about 10 carbon atoms, unsubstituted or substituted with one or more lower alkyl, lower alkoxy, nitro or amino groups or halogen atoms, wherein R' is the same or different alkylene or alkenylene radical, wherein m is an integer selected to provide an (O—R') moiety having molecular weight of from about 40 to about 6000, and wherein n and n' are the same or different integers of from 0 to about 30 inclusive, correlated with m so as to provide a hydroxy-terminated urethane compound having a molecular weight of up to about 200,000. Exemplary polymeric deposition aids of this type are generally described in U.S. Pat. No. 5,051,260, issued Sep. 24, 1991, to Chess et al.; U.S. Pat. No. 5,045,317, issued Sep. 3, 1991, to Chess et al.; and U.S. Pat. No. 4,971,800, issued Nov. 20, 1990, to Chess et al.; all of which are incorporated herein by reference.

Desirably, m will have a value of 8 and n and n' will have a value of 1 to 4 predominately. It is also desirable that the values of m, n and n' be correlated so as to provide a hydroxy-terminated urethane compound having a molecular weight of about 1,800.

An exemplary polymeric deposition aid is Topicare® Delivery Compound PP-15 (Polyolprepolymer-15) made by Penederm, Inc., Foster City, Calif. Polyolprepolymer-15 is a mixture of liquid, hydroxyl-terminated polymers in polyethylene glycol. The CAS name is poly(oxy-1,2-ethanediyl),α-hydro-ω-hydroxy-, polymer with 1,1'-methylene-bis-(4, isocyanatocyclohexane). The CTFA name is PEG-8/SMDI Copolymer.

The polymeric deposition aid should be miscible or soluble in water. Although the inventors should not be held to any particular theory of operation, miscibility of the polymeric deposition aid in water is important for the aqueous, antimicrobial liquid cleaning formulations of the present invention to function properly.

Solubility information for Polyolprepolymer-15 (PP-15) provided by Penederm Inc., is listed in Table 1.

TABLE 1

| SOLVENT | PERCENT SOLUBILITY (% w/w) |
| --- | --- |
| Water | soluble[1] |
| Alcohol (95% SDA 40-2) | 50 |
| Isopropyl Alcohol | 50 |
| Propylene Glycol | 50 |
| PEG 300 | 50 |
| Polysorbate 20 | 50 |
| Miglyol 812 | insoluble |
| Silicone (Dimethicone) | insoluble |
| Mineral Oil | insoluble |
| Ethoxydiglycol | 50 |
| Glycerine | dispersible[2] |

[1]PP-15 shows increasing aqueous solubility as temperature decreases.
[2]When a level of 1.0% or less of PP-15 was added to Glycerine, tiny droplets were observed under the microscope.

The phenol derivative antimicrobial agent may be selected from 2,4,4'-trichloro-2'-hydroxy diphenyl ether (also referred to as triclosan), 3,4,4'-trichlorocarbanilide (also referred to as triclocarban), phenoxyethanol, o-phenylphenol and o-phenylphenate). The method of the present invention has been found to work well when the phenol derivative antimicrobial agent is 2,4,4'-trichloro-2'-hydroxy diphenyl ether (triclosan) which is available under the trade name Irgasan® DP300 from Ciba-Geigy, Greensboro, N.C.

The phenol derivative antimicrobial agent is generally present in an amount ranging from about 0.1% to about 10%, by weight. Desirably, the phenol derivative antimicrobial agent is present in an amount ranging from about 0.1% to about 3%, by weight.

According to the invention, at least one nonionic surfactant and/or amphoteric surfactant is combined with the other components. Of course, a predominantly nonionic and/or amphoteric surfactant system may be used. The surfactant/surfactant system should be a nonionic surfactant and/or amphoteric surfactant that is mild to the skin and induces significantly less redness and dryness and is less disruptive to the statum corneum. It is contemplated that some anionic and/or cationic surfactants may be blended with the nonionic and/or amphoteric surfactants as long as they did not affect the mildness of the formulation. For example, the weight ratio of anionic surfactant:amphoteric surfactant is generally in the range from about 1:5 to about 20:1. As another example, the weight ratio may be from about 1:2 to about 5:1. As yet another example, the weight ratio may be from about 1:2 to about 2:1. Generally speaking, the total level of surfactants may be from about 5% to about 60% of the weight of the formulation. For example, the total level of surfactants may generally be from about 5% to 30%, desirably from about 8% to about 25%, and more desirably from about 10% to about 20% of the weight of the formulation.

Exemplary amphoteric surfactants include, but are not limited to, cocamphocarboxypropionate, cocamphocarboxy propionic acid, cocamphoacetate and cocamphodiacetate. Generally speaking, commercially available amphoteric surfactants of this type are made and sold in the form of electroneutral complexes with, for example, hydroxide counterions or with anionic sulfate or sulfonate surfactants. Suitable commercial products include, but are not limited to, products sold under the trade names of Empigen (Albright & Wilson); Miranol (Rhone-Poulenc); Alkateric (Alkaril Chemicals); Amphoterge (Lonza, Inc.); Monateric (Mona Industries); Rewoteric (Rewo Chemical Group); and Schercotic (Scher Chemicals).

Exemplary anionic surfactants include, but are not limited to ethoxylated alkyl sulfates, alkyl glyceryl ether sulfonates, methyl acyl taurates, fatty acyl glycinates, alkyl sulfosuccinates, alpha-sulfonated fatty acids, their salts and/or their esters, alkyl ethoxy carboxylates and mixtures thereof.

The surfactant systems may be composed of a combination of surfactants. For example, the surfactant systems may be composed of a mixture of one or more anionic surfactants with nonionic, amphoteric and/or betaine surfactants. Various conventional surfactant systems are commercially available and are known to those of skill in the art.

Suitable surfactant systems include Miracare MS-1 (available from Rhone-Poulenc, Cranbury, N.J.) and Standamox CAW (available from Henkel Corp., Hoboken, N.J.) and combinations thereof. Miracare MS-1 includes PEG 80 sorbitan laurate, sodium trideceth sulfate, PEG 150 distearate and lauroamphodiacetate in a water base (approximately 60%, by weight, water). Standamox CAW includes cocamidopropylamine oxide in a water base (approximately 70%, by weight, water). It is contemplated that other individual surfactants and/or surfactant systems noted for their mildness may be used.

Other suitable surfactant systems may include components such as, for example, sodium cocoyl isothionate, sodium laureth sulfate, ammonium sulfate, cocamidopropyl betaine, ammonium lauryl sulfate, PEG 80 sorbitan laurate, and/or sodium trideceth sulfate.

One or more other conventional formulating component or components may be combined with the polymeric deposition aid, phenol derivative antimicrobial agent and surfactant or surfactant system. For example, carriers, preservatives, humectants, solvents, emollients and the like may be combined with the conventional formulating components.

Generally speaking, the carrier used for the formulations of the present invention is water. The carrier may include, viscosity modifiers, thickeners, colorants, fragrances, emollients and/or buffers and/or pH control agents. For example, an exemplary additive to the carrier is polyquaternium-10, available under the trade name Polymer Ucare JR 400 from Amerchol, Edison, N.J.

Useful humectants include, for example, glycerine. Useful preservatives include, for example, DMDM Hydantoin which is available under the trade name Glydant XL 1000 from Lonza, Inc. of Fairlawn, N.J. Preservative enhancers such as, for example, Tetrasodium ETDA may also be added to the formulation.

An exemplary formulation may originate as a water phase, a surfactant phase, a preservative phase and an active phase that are blended together utilizing conventional mixing techniques to produce the aqueous, antimicrobial liquid cleaning formulation.

The water phase may be composed of sterile, deionized water and may include additives such as for example Ucare JR 400.

The surfactant phase contains one or more nonionic or amphoteric surfactants or surfactant systems. It is contemplated that the surfactant phase may include minor amounts of cationic or anionic surfactants. The surfactant phase may also contain the polymeric deposition aid. Desirably, the surfactant phase may contain surfactant systems such as, for example, Miracare MS-1, Standamox CAW, and the like.

The preservative phase may contain glycerine and preservatives and preservative enhancers such as, for example, DMDM Hydantoin, Tetrasodium EDTA, and the like.

The active phase contains the phenol derivative antimicrobial agent and may also include additional nonionic surfactant and a fragrance. Desirably, the active phase contains triclosan as the antimicrobial agent. The nonionic surfactant may be Polysorbate 40, NF, available under the trade designation Tween 40 from ICI Specialty Chemicals, Wilmington, Del. An exemplary fragrance is Elias Fragrance #16783 available from the Elias Fragrance Company.

Generally speaking, the water phase is heated to about 65° C. and the surfactant phase is blended into the water phase with stirring. Next, the preservative phase is blended into the mixture with stirring and then the active phase is added last. The pH is usually adjusted to between 6.5 and 7 using citric acid and the mixture is stirred thoroughly. Exemplary formulations of an embodiment of the invention are given in Table 2.

TABLE 2

Exemplary Formulations

| INGREDIENT | Percent Composition (Broad Range) | Percent Composition (Narrower Range) |
|---|---|---|
| WATER PHASE | | |
| Deionized water | 20.0 to 75.0 | 25.0 to 35.0 |
| Ucare JR 400 | 0.05 to 0.5 | 0.1 to 0.25 |
| SURFACTANT PHASE | | |
| Miracare MS-1 | 20.0 to 50.0 | 40.0 to 50.0 |
| Standamox CAW | 2.0 to 10.0 | 4.0 to 6.0 |
| Topicare PP-15 | 0.5 to 5.0 | 1.0 to 3.0 |
| Amercil 357 | 0.0 to 1.0 | 0.0 to 1.0 |
| PRESERVATIVE PHASE | | |
| Glycerine | 1.0 to 10.0 | 5.0 to 10.0 |
| DMDM Hydantoin | 0.4 or as needed | 0.4 or as needed |
| Tetrasodium EDTA | 0.1 or as needed | 0.1 or as needed |
| ACTIVE PHASE | | |
| Triclosan | 0.1 to 1.0 | 0.5 to 1.0 |
| Tween 40 | 1.0 to 5.0 | 1.0 to 3.0 |
| Fragrance | 0.0 to 0.3 | 0.0 to 0.1 |

According to the invention, these aqueous, antimicrobial liquid cleaning formulations provides at least about 10 percent greater (e.g., 20 percent greater or more) antimicrobial activity than the same formulation without the polymeric deposition aid. These formulations may also provide at least about 10 percent greater antimicrobial activity in combination with less skin irritation or erythema as determined by the Arm Wash Test than formulations containing anionic surfactants without the polymeric deposition aid or even the same formulation without the polymeric deposition aid. Desirably, the liquid cleaning formulations of the present invention provide at least about 10 percent greater antimicrobial activity in combination with at least about 10 percent less incidence of dermal erythema as determined by the Arm Wash Test than formulations containing anionic surfactants without the polymeric deposition aid or even the same formulation without the polymeric deposition aid. For example, the liquid cleaning formulation may provide at least about 10 percent greater antimicrobial activity in combination with at least about 15 percent less incidence of dermal erythema as determined by the Arm Wash Test than formulations containing anionic surfactants without the polymeric deposition aid or even the same formulation without the polymeric deposition aid.

EXAMPLES

Formulation

The following examples describe aqueous, antimicrobial liquid cleaning formulations. Generally speaking, the ingredients are identified by their chemical name, CFTA name, or in some cases, by their trade names. The ingredients were combined by conventional mixing and/or soap formulating techniques. The specific amounts of ingredients for Examples 1–5 are identified in Table 3.

TABLE 3

Percent Composition

| | Example 1 | Example 2 | Example 3 | Example 4 | Example 5 |
|---|---|---|---|---|---|
| WATER PHASE | | | | | |
| Deionized water | 30.2 | 29.2 | 29.2 | 27.2 | 25.2 |
| Ucare JR 400 | 0.2 | 0.2 | 0.2 | 0.2 | 0.2 |
| SURFACTANT PHASE | | | | | |
| Miracare MS-1 | 50.0 | 50.0 | 50.0 | 50.0 | 50.0 |
| Standamox CAW | 5.0 | 5.0 | 5.0 | 5.0 | 5.0 |
| Topicare PP-15 | 0.0 | 0.0 | 1.0 | 3.0 | 5.0 |
| Amercil 357 | 0.0 | 1.0 | 0.0 | 0.0 | 0.0 |

TABLE 3-continued

Percent Composition

|  | Example 1 | Example 2 | Example 3 | Example 4 | Example 5 |
|---|---|---|---|---|---|
| PRESERVATIVE PHASE | | | | | |
| Glycerine | 10.0 | 10.0 | 10.0 | 10.0 | 10.0 |
| DMDM Hydantoin | 0.4 | 0.4 | 0.4 | 0.4 | 0.4 |
| Tetrasodium EDTA | 0.1 | 0.1 | 0.1 | 0.1 | 0.1 |
| ACTIVE PHASE | | | | | |
| Triclosan | 1.0 | 1.0 | 1.0 | 1.0 | 1.0 |
| Tween 40 | 3.0 | 3.0 | 3.0 | 3.0 | 3.0 |
| Fragrance | 0.1 | 0.1 | 0.1 | 0.1 | 0.1 |

The general procedure for combining the ingredients utilized conventional techniques. A water phase was prepared by adding polymer Ucare JR 400 to deionized water at room temperature. Generally speaking, sufficient time was allowed for dispersion of polymer Ucare JR 400 (e.g., about 10 minutes). The water phase was then heated to 65° C.

In three separate vessels the surfactant phase, the preservative phase and the active phase were each pre-mixed. The surfactant phase was prepared by mixing Miracare MS-1 with Standamox CAW and Topicare PP-15. Other optional ingredients such as, for example, Amercil 357 were added to the surfactant phase at this point. Thus, the surfactant phase contained the polymeric delivery aid and the surfactant.

The preservative phase was prepared by combining glycerine with DMDM Hydantoin and Tetrasodium EDTA.

The active phase was prepared by combining triclosan with Tween 40 and a fragrance.

After the water phase reached a temperature of 65° C., the surfactant phase was added to the water phase with slow stirring.

The combined water phase and surfactant phase was maintained at a temperature of 50° C. while the preservative phase was added with stirring.

Next, the combined water phase, surfactant phase and preservative phase was maintained at a temperature of 40° C. while the active phase with stirring.

The pH of the mixture was checked and adjusted to a pH between 6.5 and 7 with addition of small amounts of a 5% solution of citric acid. The mixture was stirred at a high stirring speed overnight during which time it cooled to room temperature.

Antimicrobial Activity

Aqueous, antimicrobial liquid cleaning formulations were tested to measure their antimicrobial effects. These antimicrobial effects were compared to control formulations and conventional liquid soaps both with and without antimicrobial ingredients.

Antimicrobial effects were measured utilizing R.O.D.A.C. (Replicate Organism Detection and Counting) plates. These plates are 65×15 mm dishes specially designed to allow a raised convex surface of culture medium. Lecithin and Polysorbate 80 are incorporated in the culture medium to inactivate residual chemicals on the hands that would interfere with growth of microorganisms in the culture dish.

The three types of culture media are: Trypticase Soy Agar (TSA), MacConkey Agar (MAC), and Sabouraud Dextrose Agar (SDA). Each media contained approximately 0.7 g.L of lecithin and 5.0 g/L of Polysorbate 80.

The TSA media was used to grow gram positive bacteria that may be present on the thumb The MAC media was used to grow gram negative bacteria that may be present on the middle finger. The SDA media was used to grow yeast and molds that may be present on the palm of the hand.

The procedure was: 1) contact the target area with the specific R.O.D.A.C. media to develop an initial count of the microorganism; 2) wet and wash hands for 1 minute followed by drying with a paper towel; and 3) contact the target area with the specific R.O.D.A.C. media to develop an after-washing count of the microorganism. The percentage decrease was calculated by subtracting the count of step 3 from the count of step 1 and dividing that value by the count of step 1. This procedure was repeated for several test participants and an average value was calculated.

The liquid cleaning formulations of Example 1 and Example 3 were tested along with the following commercially available liquid soaps: Dial® Antibacterial Soap, Lever 2000®, Operating Room Scrub, Sanifresh Soap with 1.25% parachlorometaxylenol (PCMX). Three non-antibacterial soaps were also tested. They were as follows: Softsoap®, Sanifresh Premium, and Eurobath®. The results are reported in Table 4.

TABLE 4

| Material Tested | Percent Decrease in Microbial Colony Number (all) | Percent Decrease in Microbial Colony Number (gram negative bacteria only) |
|---|---|---|
| Example 3 | 60 | 55 |
| Example 1 | 0 | 0 |
| Dial ® Soap | 40 | 38 |
| Lever 2000 ® | 28 | 20 |
| O–R Scrub | 45 | 50 |
| Sani-Fresh 1.25% PCMX | 50 | 62 |
| Softsoap ® | 0 | 0 |
| Sani-Fresh Premium | 0 | 0 |
| Eurobath ® | 0 | 0 |

The R.O.D.A.C. (Replicate Organism Detection and Counting) plates test described above (but with a different data reporting procedure) was used to study the effect of adding a polymeric delivery aid to a aqueous, antimicrobial liquid cleaning formulation that includes mild surfactants which may decrease antimicrobial activity. The formulation of Example 1 was used as the control. The formulation of Example 3 containing 1.0%, by weight, Topicare® Delivery Compound PP-15 was used as the test. The results are reported in Table 5. The Percent Decrease in Microbial Colony Number values reported in Table 5 were calculated as described above except that negative numbers were zeroed for averaging. This generates a greater percentage decrease for poorer performing formulations that are likely to have microbial growth instead of a decrease. Average values calculated in this manner provide a more conservative comparison of products that perform well (i.e., provide large decreases in microbial growth)

TABLE 5

| Organism | Example 1 % Decrease | Example 3 % Decrease |
|---|---|---|
| gram (+) bacteria | 38 | 50 |
| gram (−) bacteria | 18 | 39 |
| yeast/mold | 16 | 39 |

The R.O.D.A.C. (Replicate Organism Detection and Counting) plates test described was compare the antimicrobial activity of commercially Lever 2000® Liquid Antibacterial soap with the formulation of Example 3. The results are reported in Table 6. The Percent Decrease in Microbial Colony Number values reported in Table 6 were calculated as described above with the negative numbers included for averaging.

TABLE 6

| Organism | Lever 2000 ® % Decrease | Example 3 % Decrease |
|---|---|---|
| gram (+) bacteria | 35 | 50 |
| gram (−) bacteria | 30 | 39 |
| yeast/mold | 34 | 39 |

Repeat Insult Patch Test

An occluded repeat insult patch test was conducted to evaluate the dermal tolerance of various liquid cleaning formulations. The test procedure is essentially as described by Draize, J. H., Woodward, G., and Calvery, H. D.; *Methods for the Study of Irritation and Toxicity of Substances Applied Topically to Skin and Mucous Membranes, J. Pharmacol. Exptl. Therap.* 83:377–390, 1944; and Shelanski, H. A. and Shelanski, M. V.; *A New Technique of Human Patch Tests, Proc. Sci. Sect. Toilet Goods Assoc.* 19:46–49, 1953. Generally speaking, the procedure was conducted in two phases. A primary/activation phase was conducted to determine the primary irritating potentialities of the material on initially intact skin. This phase required a 24 hour application/examination cycle that was conducted twelve times over the course of three weeks. The primary/activation phase was followed by a two week recess period. The recess period was followed by a one week challenge phase requiring a 24 hour application/examination cycle that was conducted four times.

The liquid cleaning formulations of Example 1 and Example 3 were tested along with the following commercially available liquid soaps: Dial® Antibacterial Soap, Lever 2000®, Operating Room Scrub, Sanifresh Soap with 1.25% PCMX. Three non-antibacterial soaps were also tested. They were as follows: Softsoap®, Sanifresh Premium, and Eurobath®. The results are reported in Table 7. Irritation was reported as a percentage of participants that experienced a detectable change in skin condition as determined by a trained evaluator. The responses were characterized on a scale of 1–4 as follows: 1) none; 2) faint erythema; 3) moderate erytherma; 4) intense erythema; and 4) erythema plus induration. Results are reported in Table 7. The column headed "%=2@2 weeks" reports the percentage of test participants having a response of 2 or faint erythema during the two weeks. The column headed "%=2@3 weeks" reports the percentage of test participants having a response of 2 or faint erythema during the three weeks. The column headed "%=3 or greater" reports the percentage of test participants having a response of 3 or greater during the three weeks.

TABLE 7

| Material Tested | % = 2 @ 2 Weeks | % = 2 @ 3 Weeks | % = 3 or greater |
|---|---|---|---|
| Example 3 | 3.0 | 7.8 | 0.4 |
| Example 1 | 3.5 | 10.0 | 0.7 |
| Dial ® Soap | 28.7 | 40.1 | 5.8 |
| Lever 2000 ® | 19.4 | 29.8 | 2.3 |
| Softsoap ® | 8.5 | 13.5 | 0.7 |
| Sani-Fresh Premium | 40.0 | — | (17.7) |
| Eurobath ® | 30.0 | — | (2.0) |

Referring to Table 7, tests of Sani-Fresh Premium and Eurobath® liquid soaps were suspended after two weeks due to very high levels of skin irritation. The values reported in parenthesis for those products in the column headed "%=3 or greater" are the percentage of test participants having a response of 3 or greater during the two weeks since those products were not tested for three weeks.

More detailed response data for the occluded repeat insult patch test described above is reported in Table 8. The data focus on the dermal tolerance of Dial® Liquid Antibacterial soap, Lever 2000® Liquid Antibacterial soap and the mild formulation of Example 3 containing 1%, by weight, polymeric delivery aid. In particular, the data focus on the dermal response during the 3 week primary activation phase and the 1 week challenge phase (which separated from the primary phase by a 2 week rest period). The responses were characterized as: 1) none; 2) faint erythema; 3) moderate erytherma; 4) intense erythema; and 4) erythema plus induration.

TABLE 8

| | Dial ® Soap | | Lever 2000 ® | | Example 3 | |
|---|---|---|---|---|---|---|
| Response | Primary | Chllng. | Primary | Chllng. | Primary | Chllng. |
| None | 8 | 68 | 10 | 72 | 48 | 88 |
| Faint erythema | 8 | 14 | 18 | 14 | 32 | 3 |
| Moderate erythema | 44 | 8 | 50 | 5 | 15 | 0 |
| Intense erythema + indur. | 9 | 1 | 8 | 0 | 1 | 0 |
| | 32 | 0 | 15 | 0 | 5 | 0 |

Exaggerated Arm Wash Study

The irritation potential of the mild formulation of Example 3 containing 1%, by weight, polymeric delivery aid was evaluated relative to Lever 2000® Liquid Antibacterial soap utilizing the Arm Wash Test. This testing technique is described by Sharko, P. T.; Murahata, R. I.; Leyden, J. J.; and Grove, G. L., *Arm Wash with Instrumental Evaluation-A Sensitive Technique for Differentiating the Irritation Potential of Personal Washing Products; J. Dermal Clinical Eval. Soc.,* Volume 2, No. 1, pps. 19–27 (September 1991).

Irritation potential was assessed by measurement of skin dryness, stratum corneum barrier function (TEWL), and erythema. Skin barrier function was assessed utilizing a ServoMed Evaporimeter. Water content of the skin (i.e., skin dryness) was measured utilizing an IBS Skin Surface Hygrometer (available under the trade name Skicon 200).

Skin color was measured utilizing a Minolta Chroma Meter and the CIELAB L*, a*, b* coordinate system. Expert graders and self-assessment by test participants scores were also used to evaluate the irritation potential.

Irritation was measured following application of each formulation to the ventral side of one arm. Four (4) applications per day over a period of five (5) days were used. Paired statistical analysis between formulations was conducted by comparison between contralateral sites of 14 test participants. The results are reported graphically in FIGS. 1–5. In each of FIGS. 1–5, the mild formulation of Example 3 containing 1%, by weight, polymeric delivery aid is identified as Code (600/3) and Lever 2000® Liquid Antibacterial soap is identified as Code (400/3).

Figure 1:
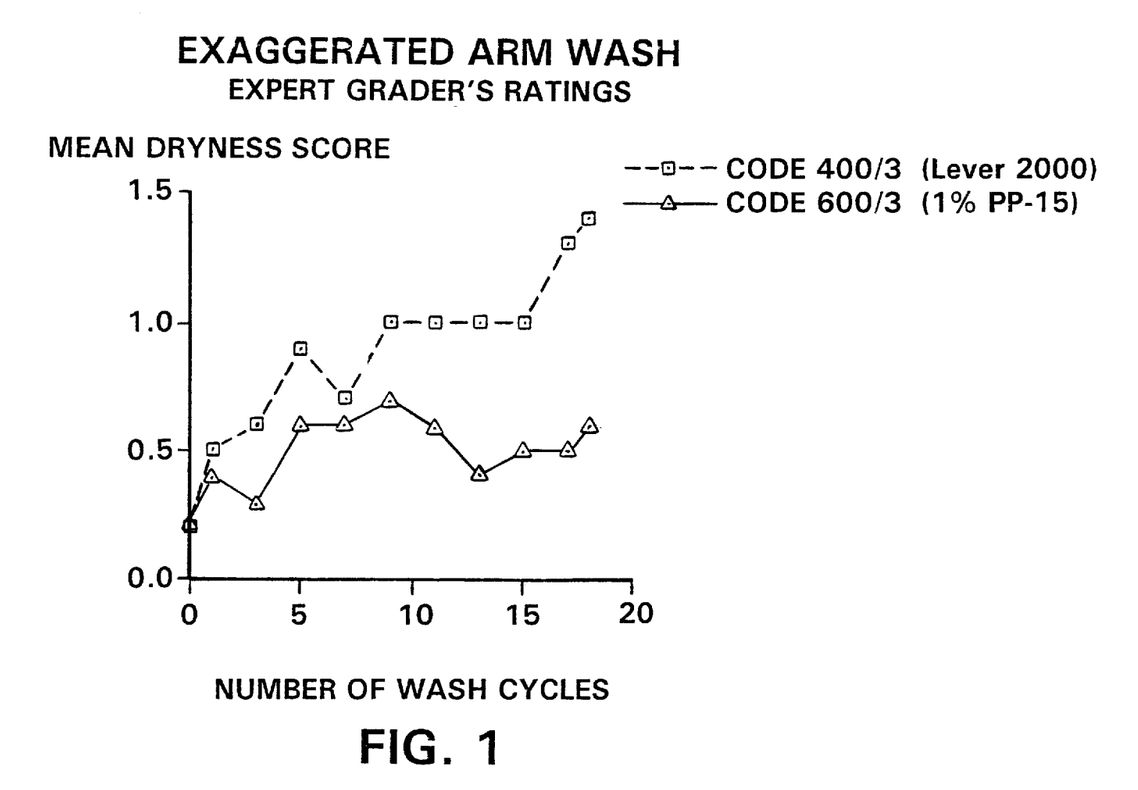
FIG. 1 is a plot of data from an Arm Wash Test of exemplary aqueous, antimicrobial liquid cleaning formulations.
Figure 2:
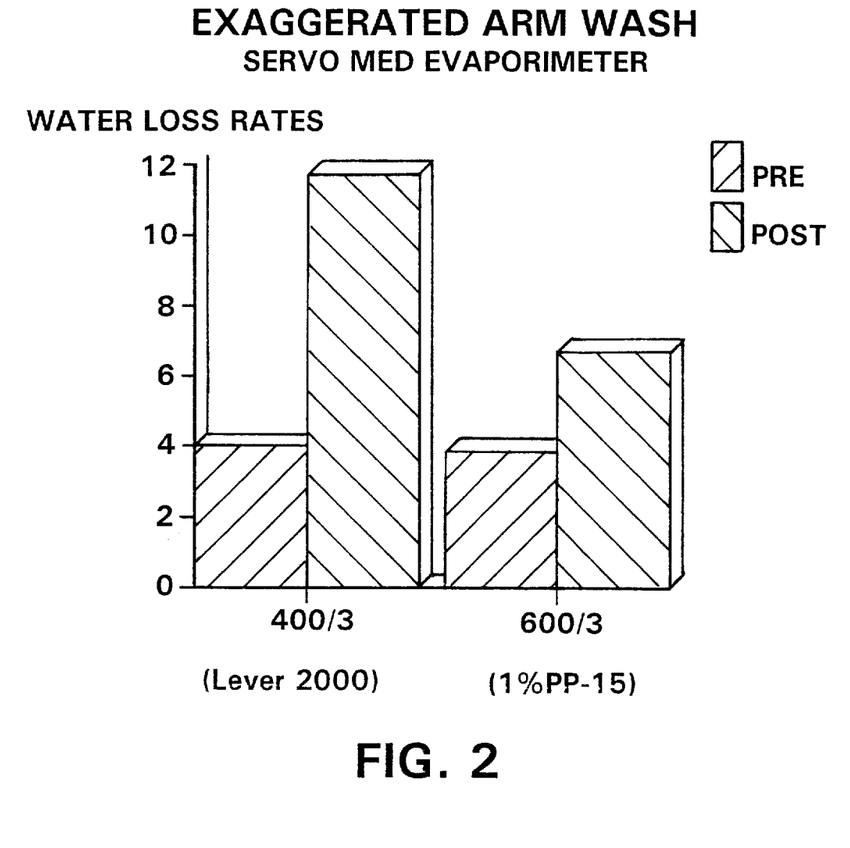
FIG. 2 is a representation of data from an Arm Wash Test of exemplary aqueous, antimicrobial liquid cleaning formulations.
Figure 3:
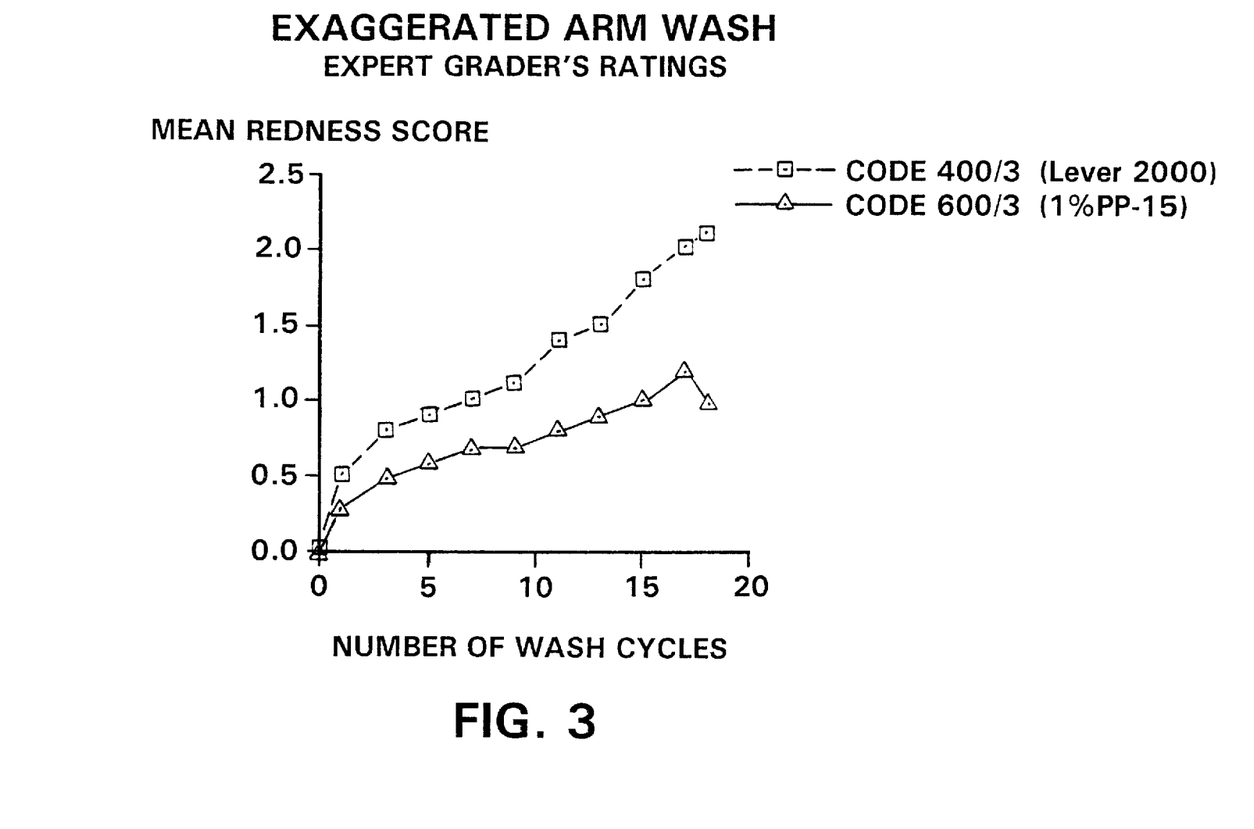
FIG. 3 is a plot of data from an Arm Wash Test of exemplary aqueous, antimicrobial liquid cleaning formulations.
Figure 4:
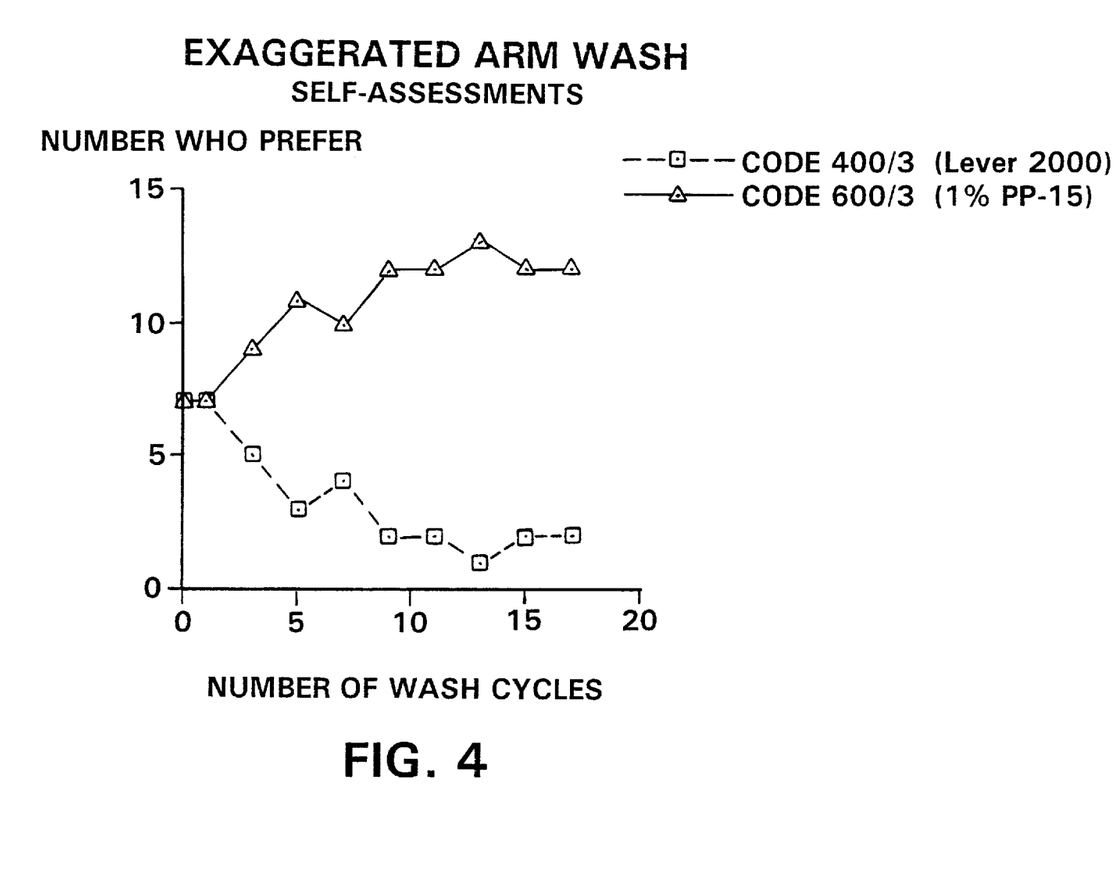
FIG. 4 is a plot of data from an Arm Wash Test of exemplary aqueous, antimicrobial liquid cleaning formulations.
Figure 5:
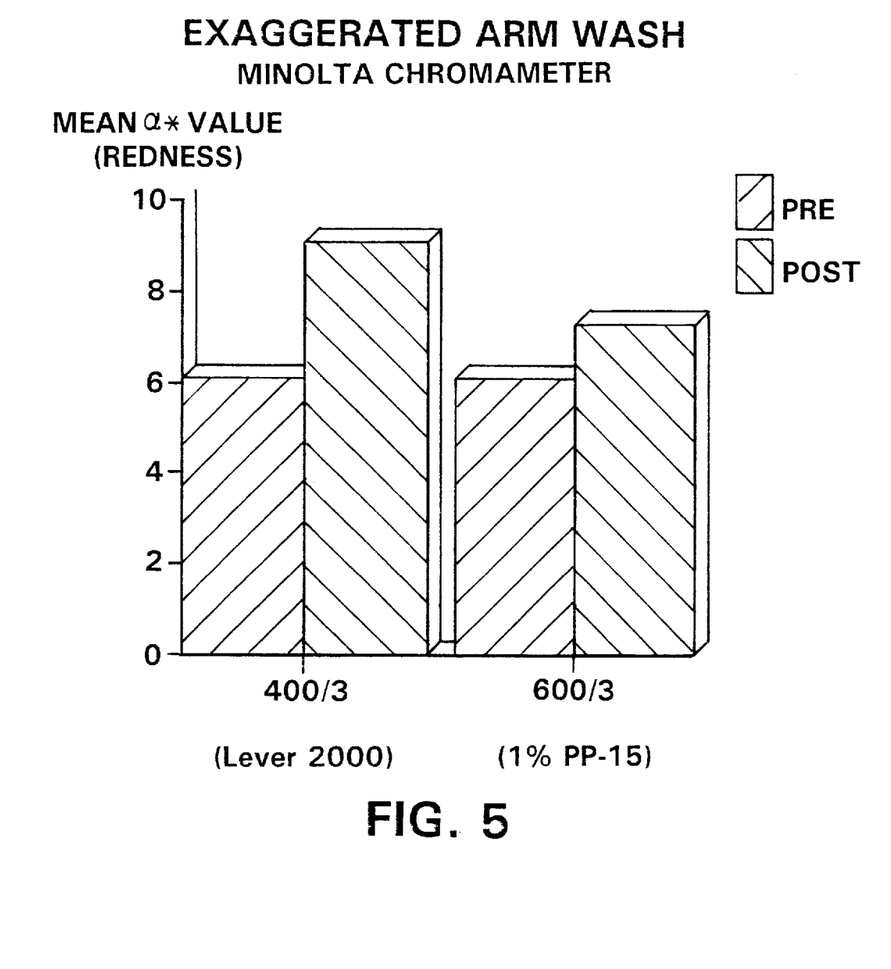
FIG. 5 is a representation of data from an Arm Wash Test of exemplary aqueous, antimicrobial liquid cleaning formulations.

FIG. 1 is a plot of the mean dryness score as determined by expert graders versus the number of wash cycles. FIG. 2 is a representation of skin water loss as determined by the ServoMed Evaporimeter prior to the study and after 5 days of applications. FIG. 3 is a plot of the mean redness score as determined by expert graders versus the number of wash cycles. FIG. 4 is a plot of the number of test participants who prefer one formulation over the other versus the number of wash cycles. FIG. 5 is a representation of skin redness value (i.e., the a* coordinate on the CIELAB system) loss as determined by the Minolta Chroma Meter prior to the study and after 5 days of applications.

As can be seen from data reported in Tables 5 and 7, the present invention provides a method of increasing the antimicrobial activity of conventional antibacterial soap formulations such as, for example, Dial® Antibacterial liquid soap and Lever 2000® liquid soap. The improvement in the Percent Decrease in Microbial Colony Number by the practice of the method of the present invention may be 10% or more. For example, the improvement may be 20%. In some cases, the improvement may be 40% or even 60% or more.

The data in Tables 4, 5 and 6 indicate the present invention provides a mild, liquid cleaning formulation that also has acceptable levels of antimicrobial activity. Without the addition of the polymeric delivery aid, the mild, liquid cleaning formulation had lower levels of antimicrobial activity. In fact, the data in Table 4 show essentially no measurable antimicrobial activity for the formulation without the polymeric delivery compound.

The mildness of the aqueous, antimicrobial liquid cleaning formulation is indicated by data in Tables 7 and 8 as well as FIGS. 1–5. In both the repeat insult patch test and the Arm Wash Test, the formulations of the present invention generated much less irritation.

While the present invention has been described in connection with certain embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An aqueous, anti-microbial liquid cleaning formulation for cleansing the skin comprising:

a polymeric deposition aid comprising a mixture of liquid, hydroxyl-terminated urethane polymers in polyethylene glycol;

an antimicrobial agent having a phenol moiety; and a surfactant system comprising predominantly nonionic surfactants, amphoteric surfactants and/or combinations thereof such that the liquid cleaning formulation provides at least about 10 percent greater antimicrobial activity than the same formulation without the polymeric deposition aid.

2. The liquid cleaning formulation of claim 1, wherein the polymeric deposition aid is a hydroxy terminated urethane compound having the formula:

wherein R is selected from an alkylene or alkenylene radical containing from one to about 20 carbon atoms, a cycloalkylene or cycloalkenylene radical containing from about 5 to about 10 carbon atoms, a mononuclear or fused ring arylene radical containing from about 6 to about 10 carbon atoms, unsubstituted or substituted with one or more lower alkyl, lower alkoxy, nitro or amino groups or halogen atoms, wherein R' is the same or different alkylene or alkenylene radical, wherein m is an integer selected to provide an (O—R') moiety having molecular weight of from about 40 to about 6000, and wherein n and n' are the same or different integers of from 0 to about 30 inclusive, correlated with m so as to provide a hydroxy-terminated urethane compound having a molecular weight of up to about 200,000.

3. The liquid cleaning formulation of claim 2, wherein m is an integer selected to provide an (O—R') moiety having molecular weight of from about 40 to about 60.

4. The liquid cleaning formulation of claim 2, wherein n and n' are the same or different integers of from 0 to about 30 inclusive, correlated with m so as to provide a hydroxy-terminated urethane compound having a molecular weight of up to about 1,800.

5. The liquid cleaning formulation of claim 1, wherein the polymeric deposition aid is poly(oxy-1,2-ethanediyl),α-hydro-ω-hydroxy-, polymer with 1,1'-methylene-bis-(4, isocyanato-cyclohexane).

6. The liquid cleaning formulation of claim 1, wherein the phenol derivative antimicrobial agent is 2,4,4'-trichloro-2'-hydroxy diphenyl ether.

7. The liquid cleaning formulation of claim 1, further comprising at least one formulating component.

8. The liquid cleaning formulation of claim 7, wherein at least one formulating component is selected from the group consisting of carriers, preservatives, humectants, emollients and combinations thereof.

9. The liquid cleaning formulation of claim 1, wherein the formulation provides at least about 10 percent greater antimicrobial activity than formulations containing predominantly anionic surfactants or cationic surfactants or combinations thereof and lacking the polymeric deposition aid.

10. The liquid cleaning formulation of claim 1, wherein the formulation provides at least about 10 percent greater antimicrobial activity in combination with less skin irritation as determined by the Arm Wash Test than formulations containing predominantly anionic surfactants, cationic surfactants or combinations thereof and lacking the polymeric deposition aid.

11. The liquid cleaning formulation of claim 1, wherein the formulation provides at least about 10 percent greater antimicrobial activity in combination with at least about 10 percent less incidence of dermal erythema as determined by the Arm Wash Test than formulations containing predominantly anionic surfactants, cationic surfactants or combinations thereof and lacking the polymeric deposition aid.

12. An aqueous, antimicrobial liquid cleaning formulation for cleansing the skin comprising:

a polymeric deposition aid comprising a mixture of liquid, hydroxyl-terminated urethane polymers in polyethylene glycol;

an antimicrobial agent having a phenol moiety; and a surfactant system comprising predominantly nonionic surfactants, amphoteric surfactants and/or combinations thereof such that the liquid cleaning formulation provides at least about 10 percent greater antimicrobial activity in combination with less skin irritation as determined by the Arm Wash Test than formulations containing predominantly anionic surfactants, cationic surfactants or combinations thereof and lacking the polymeric deposition aid.

13. The liquid cleaning formulation of claim 12, wherein the polymeric deposition aid is a hydroxy terminated urethane compound having the formula:

wherein R is selected from an alkylene or alkenylene radical containing from one to about 20 carbon atoms, a cycloalkylene or cycloalkenylene radical containing from about 5 to about 10 carbon atoms, a mononuclear or fused ring arylene radical containing from about 6 to about 10 carbon atoms, unsubstituted or substituted with one or more lower alkyl, lower alkoxy, nitro or amino groups or halogen atoms, wherein R' is the same or different alkylene or alkenylene radical, wherein m is an integer selected to provide an (O—R') moiety having molecular weight of from about 40 to about 6000, and wherein n and n' are the same or different integers of from 0 to about 30 inclusive, correlated with m so as to provide a hydroxy-terminated urethane compound having a molecular weight of up to about 200,000.

14. The liquid cleaning formulation of claim 13, wherein m is an integer selected to provide an (O—R') moiety having molecular weight of from about 40 to about 60.

15. The liquid cleaning formulation of claim 13, wherein n and n' are the same or different integers of from 0 to about 30 inclusive, correlated with m so as to provide a hydroxy-terminated urethane compound having a molecular weight of up to about 1,800.

16. The liquid cleaning formulation of claim 12, wherein the polymeric deposition aid is poly(oxy-1,2-ethanediyl),α-hydro-ω-hydroxy-, polymer with 1,1'-methylene-bis-(4, isocyanato-cyclohexane).

17. The liquid cleaning formulation of claim 12, wherein the phenol derivative antimicrobial agent is 2,4,4'-trichloro-2'-hydroxy diphenyl ether.

18. The liquid cleaning formulation of claim 12, further comprising at least one formulating component.

19. The liquid cleaning formulation of claim 18, wherein the at least one formulating component is selected from the group consisting of carriers, preservatives, humectants, emollients and combinations thereof.

* * * * *